(12) United States Patent  
Chen

(10) Patent No.: US 8,414,474 B2  
(45) Date of Patent: Apr. 9, 2013

(54) MULTIPLE VIEW ANGLE ENDOSCOPE APPARATUS

(75) Inventor: Sung-Nan Chen, Taoyuan County (TW)

(73) Assignee: Medical Intubation Technology Corporation, Taoyuan County (TW)

( * ) Notice: Subject to any disclaimer, the term of this patent is extended or adjusted under 35 U.S.C. 154(b) by 231 days.

(21) Appl. No.: 13/009,219

(22) Filed: Jan. 19, 2011

(65) Prior Publication Data

US 2011/0263942 A1 Oct. 27, 2011

(30) Foreign Application Priority Data

Apr. 23, 2010 (TW) ................................ 99112997 A

(51) Int. Cl.  
*A61B 1/05* (2006.01)
(52) U.S. Cl. .................... 600/109; 600/129; 600/170
(58) Field of Classification Search .................. 600/129, 600/111, 170, 173, 166, 112, 109; 348/65.76, 348/374  
See application file for complete search history.

(56) References Cited

U.S. PATENT DOCUMENTS

| | | | |
|---|---|---|---|
| 5,010,876 A * | 4/1991 | Henley et al. ................. | 600/112 |
| 5,609,561 A * | 3/1997 | Uehara et al. ................. | 600/112 |
| 5,940,126 A * | 8/1999 | Kimura ......................... | 348/294 |
| 6,450,950 B2 * | 9/2002 | Irion ............................. | 600/170 |
| 6,561,972 B2 * | 5/2003 | Ooshima et al. ............. | 600/173 |
| 6,945,929 B2 * | 9/2005 | Ando ............................ | 600/111 |
| 7,108,657 B2 * | 9/2006 | Irion et al. ................... | 600/110 |
| 7,967,745 B2 * | 6/2011 | Gilad ........................... | 600/160 |
| 7,976,459 B2 * | 7/2011 | Laser ........................... | 600/109 |
| 8,289,381 B2 * | 10/2012 | Bayer et al. ..................... | 348/65 |
| 2003/0025824 A1 * | 2/2003 | Ishikawa ...................... | 348/374 |
| 2004/0171914 A1 * | 9/2004 | Avni ............................ | 600/160 |
| 2007/0126923 A1 * | 6/2007 | Shinomiya .................... | 348/374 |
| 2007/0203396 A1 * | 8/2007 | McCutcheon et al. ........ | 600/173 |
| 2009/0105538 A1 * | 4/2009 | Van Dam et al. ............. | 600/109 |
| 2009/0292167 A1 * | 11/2009 | Kimoto ........................ | 600/109 |
| 2010/0286477 A1 * | 11/2010 | OuYang et al. ............... | 600/109 |
| 2011/0263938 A1 * | 10/2011 | Levy ............................ | 600/109 |

* cited by examiner

*Primary Examiner* — John P Leubecker  
(74) *Attorney, Agent, or Firm* — WPAT, P.C.; Anthony King

(57) ABSTRACT

An endoscope apparatus is disclosed, which includes a tube body, a cover, a first image capture module, a second image capture module and a connecting tube. The first image capture module captures an image with a first view, and the second image capture module captures an image with a second view. A first flexible printed circuit board (PCB) is disposed inside the tube body, and a second flexible PCB is disposed inside the connecting tube. The connecting tube is connected with the tube body via the connecting between the first flexible PCB and the second flexible PCB, so as to transmit the images captured by the first image capture module or the second image capture module.

9 Claims, 8 Drawing Sheets

MULTIPLE VIEW ANGLE ENDOSCOPE APPARATUS

FIELD OF THE INVENTION

The present invention relates to an endoscope apparatus, and more particularly to an endoscope apparatus providing two angles of view and having a small tube diameter.

BACKGROUND OF THE INVENTION

At present, one-piece tube bodies are mostly used as insertion parts of conventional endoscope apparatuses for the accommodation of printed circuit boards that are connected with image capture modules and light-emitting modules. However, as the tube diameters of endoscopes are trending towards smaller sizes, there occurs a problem that it is more and more difficult to assemble printed circuit boards, image capture modules and light-emitting modules in conventional endoscopes. Particularly in endoscope apparatuses that capture images with two angles of view, due to their higher structural complexity compared to endoscopes providing a single angle of view, the difficulty will increase as endoscopes are trending towards smaller sizes. Therefore, with more and more stringent requirements for the tube diameters of endoscopes, it is quite urgent and important to provide an endoscope apparatus having a small tube diameter and suitable for providing two angles of view even multiple angles of view.

SUMMARY OF THE INVENTION

In view of the above-mentioned problems of the prior art, an object of the present invention is to provide an endoscope apparatus, which solves the problem of difficulty in assembly of an endoscope providing two angles of view and having a small tube diameter.

According to the object of the present invention, there is provided an endoscope apparatus comprising a tube body, a first image capture module, a first flexible printed circuit board (PCB), and a second image capture module. One end of the tube body is further connected with an accommodating part. The first image capture module is disposed inside the accommodating part and comprises at least a first light-emitting device, a first lens and a first image sensor. The first light-emitting device emits light to irradiate an object. The first lens collects a reflected light with a first viewing angle reflected by the object. The first image sensor is disposed facing the first lens and adjacent to the first light-emitting device for receiving the reflected light and providing a first image signal according to the reflected light. The second image capture module is disposed inside the tube body, and is connected with the first flexible PCB, which comprises at least a second light-emitting device, a second lens and a second image sensor. The second light-emitting device is provided for emitting light to irradiate the object. The second lens is provided for collecting the other reflected light with a second viewing angle reflected by the object. The second image sensor is disposed facing the second lens and adjacent to the second light-emitting device for receiving the other reflected light and providing a second image signal according to the other reflected light.

Wherein, the endoscope apparatus further comprises a notch and a cover. The notch is disposed on one side near one end of the tube body; the cover is disposed on the notch of the tube body, the cover having a first opening and a second opening. The second light-emitting device is disposed below the first opening, and the second lens is disposed below the second opening.

Wherein, the endoscope apparatus further comprises a connecting tube and a second flexible PCB. One end of the connecting tube is connected with the other end of the tube body. The diameter of the end of the connecting tube is different from the diameter of the other end of the connecting tube. The second flexible PCB disposed inside the connecting tube. The end of the connecting tube is connected with the other end of the tube body via the connection between the first flexible PCB and the second flexible PCB.

Wherein, the first flexible PCB is further provided with a switching module for switching the first image signal or the second image signal to be outputted to the second flexible PCB.

Wherein, the endoscope apparatus further comprises a hose, a holding part and a switch. The hose is connected with the other end of the connecting tube, and at least a conducting wire is further disposed inside the hose, and the conducting wire is connected with the second flexible PCB to transmit the first image signal or the second image signal. The holding part is connected with the connecting tube via the hose. The switch has a plurality of indicator lights and is connected with the conducting wire, and the switch is disposed on the hose and located between the connecting tube and the holding part for controlling the switching module.

Wherein, the holding part further comprises a printed circuit board and a display unit. The printed circuit board is disposed inside the holding part and connected with the second flexible PCB via the at least a conducting wire for receiving the first image signal or the second image signal. The display unit is disposed on the holding part and connected with the printed circuit board for receiving the first image signal or the second image signal to display the image with the first angle of view or the image with the second angle of view.

Wherein, the first flexible PCB is further provided with a switching module for switching the first image signal or the second image signal to be outputted to the second flexible PCB.

Wherein, endoscope apparatus further comprises a hose, a holding part and a switch. The hose is connected with the other end of the tube body, and at least a conducting wire is further disposed inside the hose, and the conducting wire is connected with the first flexible PCB to transmit the first image signal or the second image signal. The holding part is connected with the tube body via the hose. The switch has a plurality of indicator lights and is connected with the at least a conducting wire, and the switch is disposed on the hose and located between the tube body and the holding part for controlling the switching module.

Wherein, the holding part further comprises a printed circuit board and a display unit. The printed circuit board is disposed inside the holding part and connected with the first flexible PCB via the at least a conducting wire for receiving the first image signal or the second image signal. The display unit is disposed on the holding part and connected with the printed circuit board for receiving the first image signal or the second image signal to display the image with the first angle of view or the image with the second angle of view.

Wherein, the first light-emitting device and the second light-emitting device are light-emitting diodes (LED), and the first light-emitting device and the second light-emitting device emit white light, red light, blue light, infrared light or ultraviolet light.

As described above, the endoscope apparatus of the present invention may have one or more of the following advantages:

(1) The endoscope apparatus of the present invention captures images with different angles, so as to increase convenience of observing an object to be inspected by an endoscope apparatus.

(2) According the endoscope apparatus, the problem of difficulty in assembly of an endoscope apparatus having a small tube diameter can be solved by the assembly of multiple components.

DETAILED DESCRIPTION OF THE PREFERRED EMBODIMENTS

Figure 1:
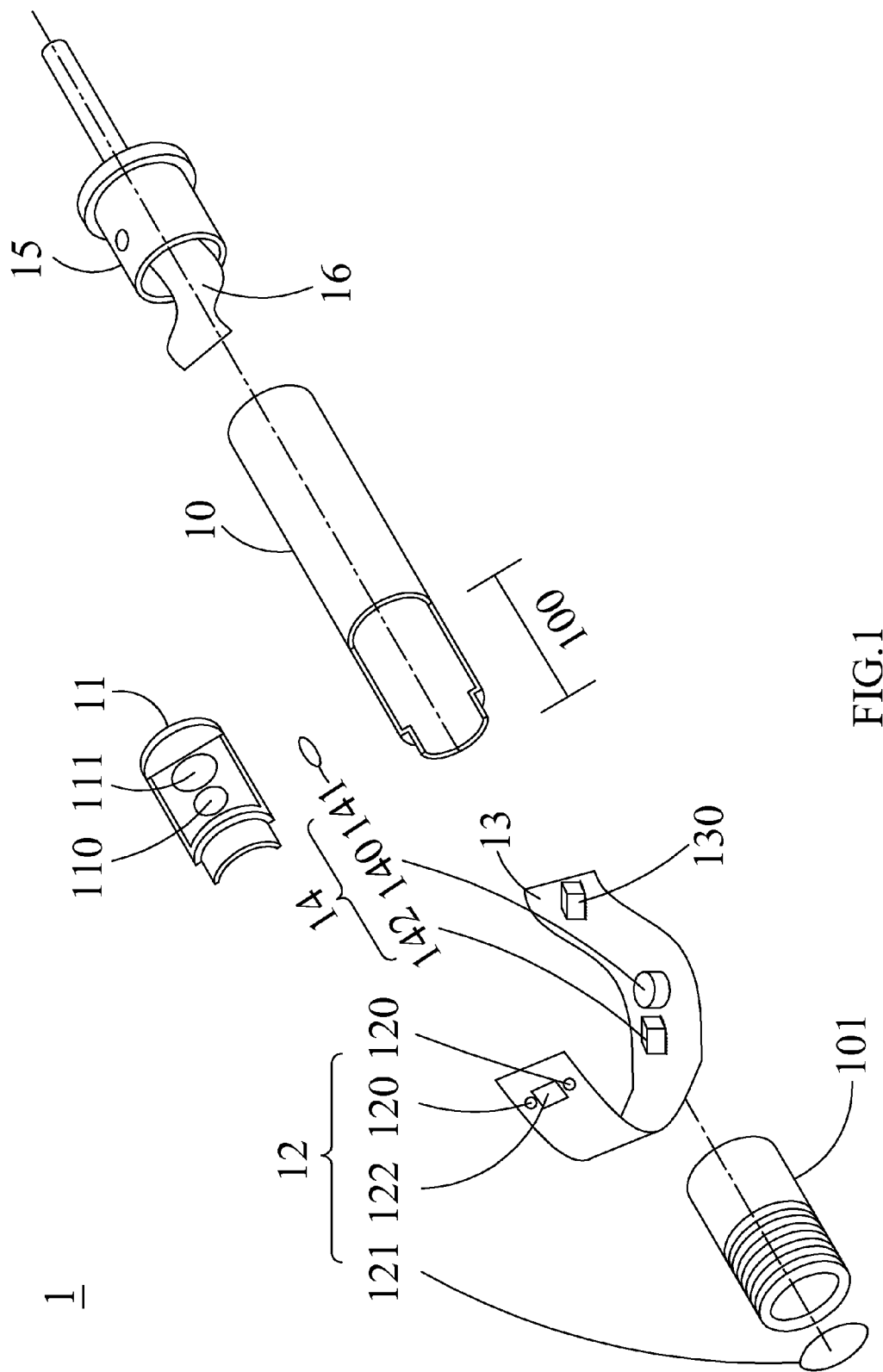
FIG. 1 is an exploded view of an endoscope apparatus according to the present invention.
Figure 2:
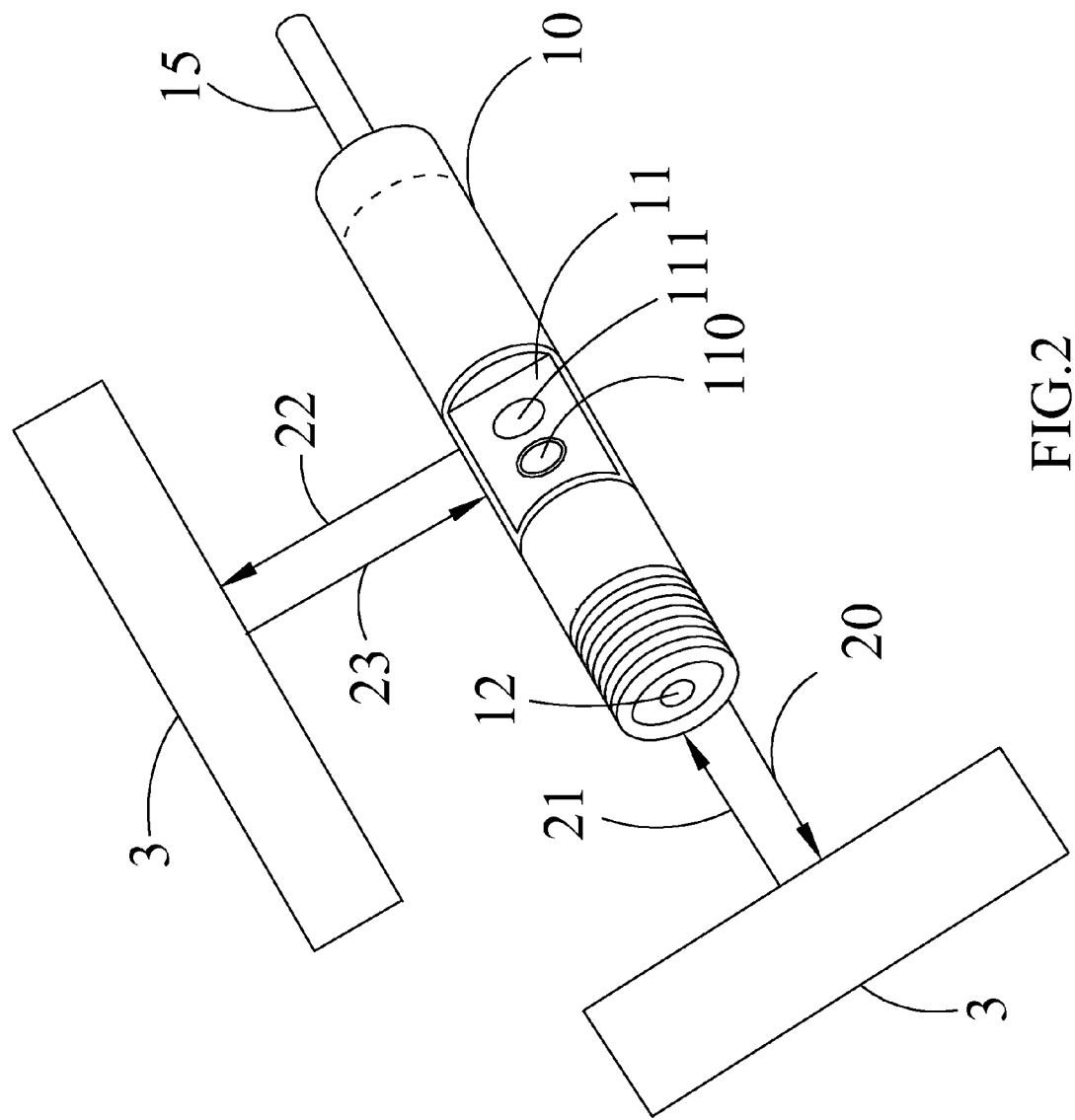
FIG. 2 is an assembly drawing of an endoscope apparatus according to the present invention.

Referring to FIGS. 1 and 2, there are shown an exploded view and an assembly drawing respectively of an endoscope apparatus according to the present invention. As shown in FIGS. 1 and 2, an endoscope apparatus 1 according to the present invention comprises a tube body 10, a cover 11, a first image capture module 12, a first flexible PCB 13, a second image capture module 14, a connecting tube 15 and a second flexible PCB 16. A notch 100 is disposed on one side near one end of the tube body 10. One end of the tube body is connected with an accommodating part 101. The cover 11 is disposed on the notch 100 of the tube body 10. The cover 11 has a circular cross-section adapted to the tube body 10, and has a first opening 110 and a second opening 111. The first image capture module 12 is disposed inside the accommodating part 101 and comprises at least a first light-emitting device 120, a first lens 121 and a first image sensor 122. The first light-emitting device 120 emits light 20 to irradiate an object 3. The first lens 121 collects a reflected light 21 with a first viewing angle reflected by the object 3. The first image sensor 122 is disposed facing the first lens 121 and the first light-emitting device 120 for receiving the reflected light 21 and providing a first image signal according to the reflected light 21. The second image capture module 14 is disposed inside the tube body 10 and below the cover 11, and is connected with the first flexible PCB 13, which comprises at least a second light-emitting device 140, a second lens 141 and a second image sensor 142. The second light-emitting device 140 is disposed below the first opening 110 for emitting light 21 to irradiate the object 3. The second lens 141 is disposed below the second opening 111 for collecting the other reflected light 23 with a second viewing angle reflected by the object 3. The second image sensor 142 is disposed facing the second lens 141 and the second light-emitting device 140 for receiving the other reflected light 23 and providing a second image signal according to the other reflected light 23. The first flexible PCB 13 is disposed inside the tube body 10 and is connected with the first image capture module 12 and the second image capture module 14. One end of the connecting tube 15 is connected with the other end of the tube body 10, and the diameter of the end of the connecting tube 15 is different from the diameter of the other end of the connecting tube 15. The second flexible PCB 16 is disposed inside the connecting tube 15. The end of the connecting tube 15 is connected with the other end of the tube body 10 via the connection between the first flexible PCB 13 and the second flexible PCB 16.

Furthermore, in some preferred embodiments, the first lens 121 and the second lens 141 may be convex lenses, concave lenses or combinations of concave and convex lenses. The first flexible PCB 13 is further provided with a switching module 130 for switching the first image signal or the second image signal to be outputted to the second flexible PCB 16. The first light-emitting device 120 and the second light-emitting device 140 may be light-emitting diodes (LED). The first light-emitting device 120 and the second light-emitting device 140 may emit white light, red light, blue light, infrared light or ultraviolet light, etc. The first image sensor 122 and the second image sensor 142 may be complementary metal-oxide-semiconductors (CMOS) or charge coupled devices (CCD).

Figure 3:
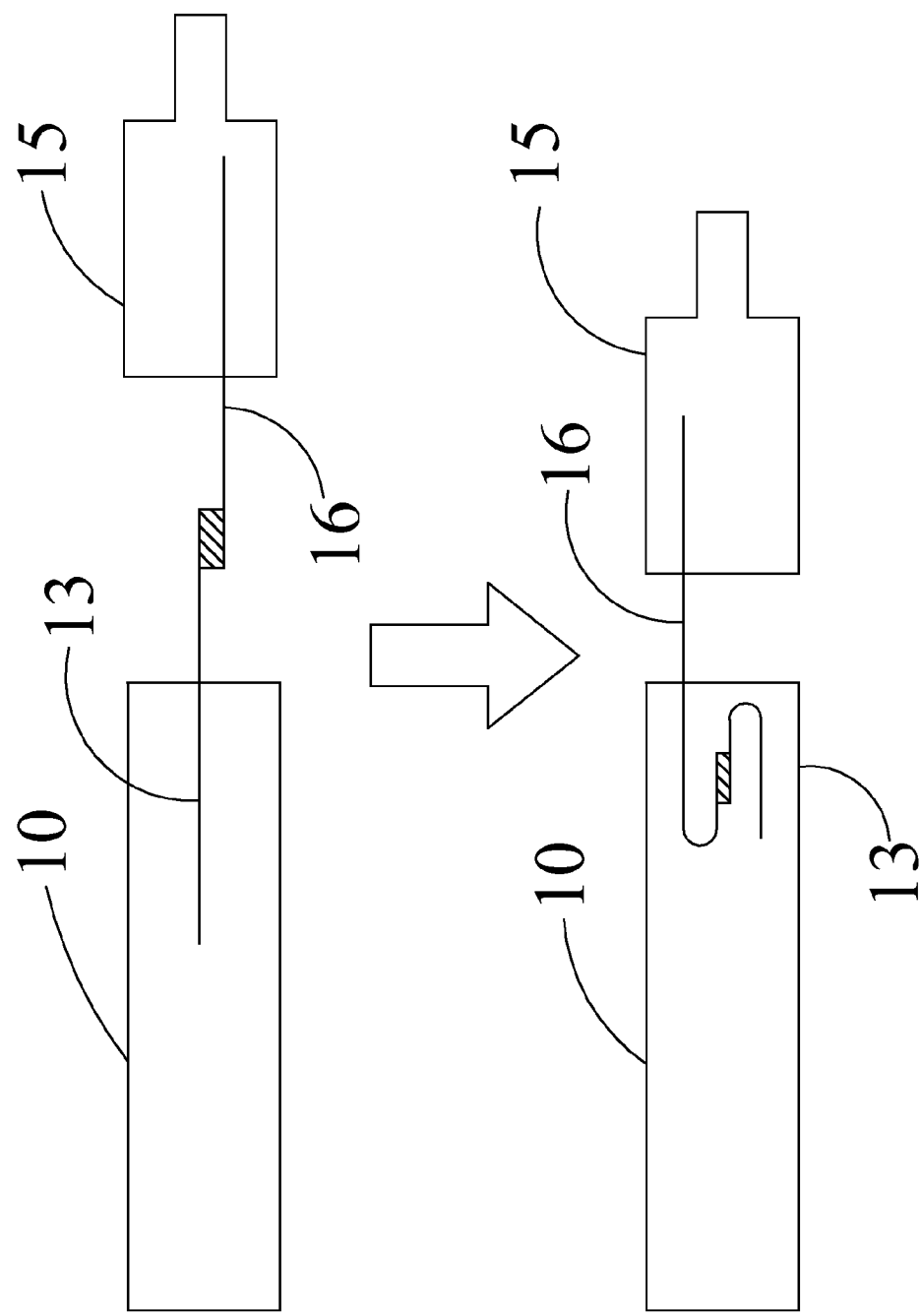
FIG. 3 is a schematic view showing the assembly of a tube body and a connecting tube of an endoscope apparatus according to the present invention.
Figure 4:
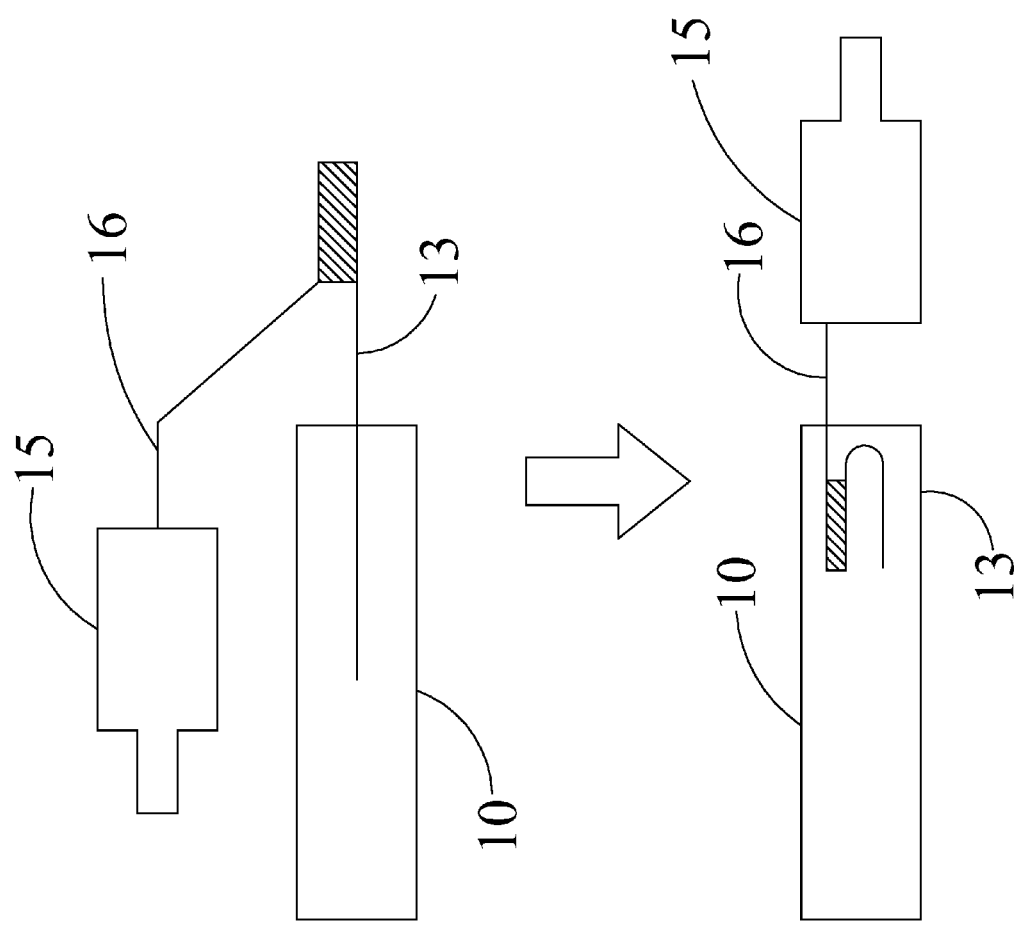
FIG. 4 is another schematic view showing the assembly of a tube body and a connecting tube of an endoscope apparatus according to the present invention.

Referring to FIG. 3, there is shown a schematic view showing the assembly of a tube body and a connecting tube of an endoscope apparatus according to the present invention. As shown in FIG. 3, the first flexible PCB 13 in this embodiment is connected with the second flexible PCB 16 in a manner that the first flexible PCB 13 is protruded out of the tube body 10 and the second flexible PCB 16 is protruded out of the connecting tube 15 and then they are connected by bonding or soldering and bent in an S configuration for inserting into the tube body 10. In another preferred embodiment, as shown in FIG. 4, the first flexible PCB 13 and the second flexible PCB 16 are connected with each other and then bent in a U configuration for inserting into the tube body 10.

Figure 5:
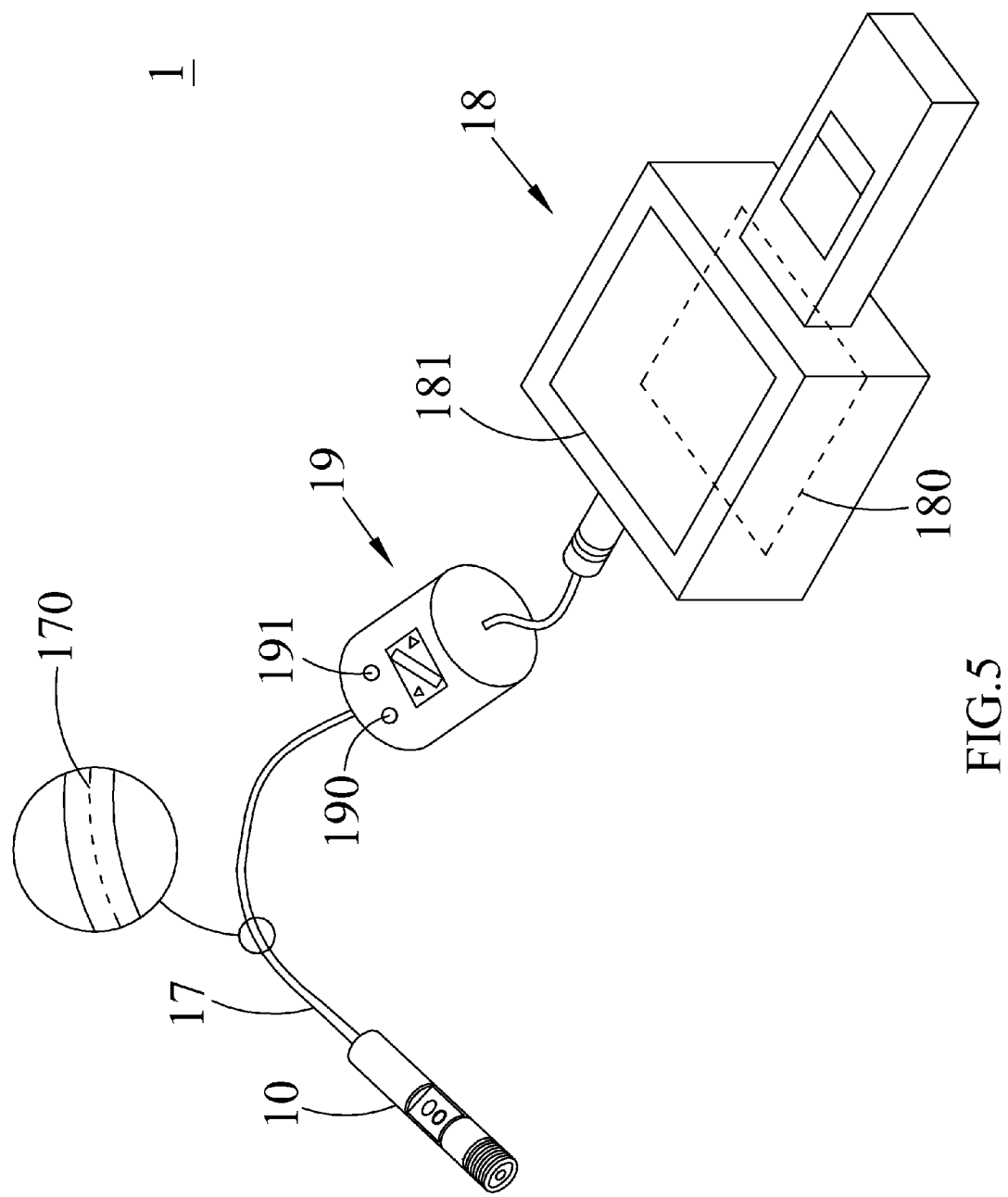
FIG. 5 is a schematic view of a preferred embodiment of an endoscope apparatus according to the present invention.

Referring to FIG. 5, there is shown a schematic view of a preferred embodiment of an endoscope apparatus according to the present invention. As shown in FIG. 5, an endoscope apparatus 1 according to the present invention further comprises a hose 17, a holding part 18 and a switch 19. The hose 17 is connected with the other end of the connecting tube 15. At least a conducting wire 170 is further disposed inside the hose 17, and the conducting wire 170 is connected with the second flexible PCB 16 to transmit the first image signal or the second image signal. The holding part 18 is connected with the connecting tube 15 via the hose 17, and comprises a printed circuit board 180 and a display unit 181. The printed circuit board 180 is disposed inside the holding part 18 and connected with the second flexible PCB 16 via the conducting wire 170 for receiving the first image signal or the second image signal. The display unit 181 is disposed on the holding part 18 and connected with the printed circuit board 180 for receiving the first image signal or the second image signal to display the image with the first angle of view or the image with the second angle of view. In this embodiment, the display unit 181 may be a liquid crystal display (LCD). Moreover, the switch 19 has a plurality of indicator lights 190, 191 and is connected with the at least a conducting wire 170. The switch 19 is disposed on the hose 17 and located between the connecting tube 15 and the holding part 18 for controlling the switching module 130.

Figure 6:
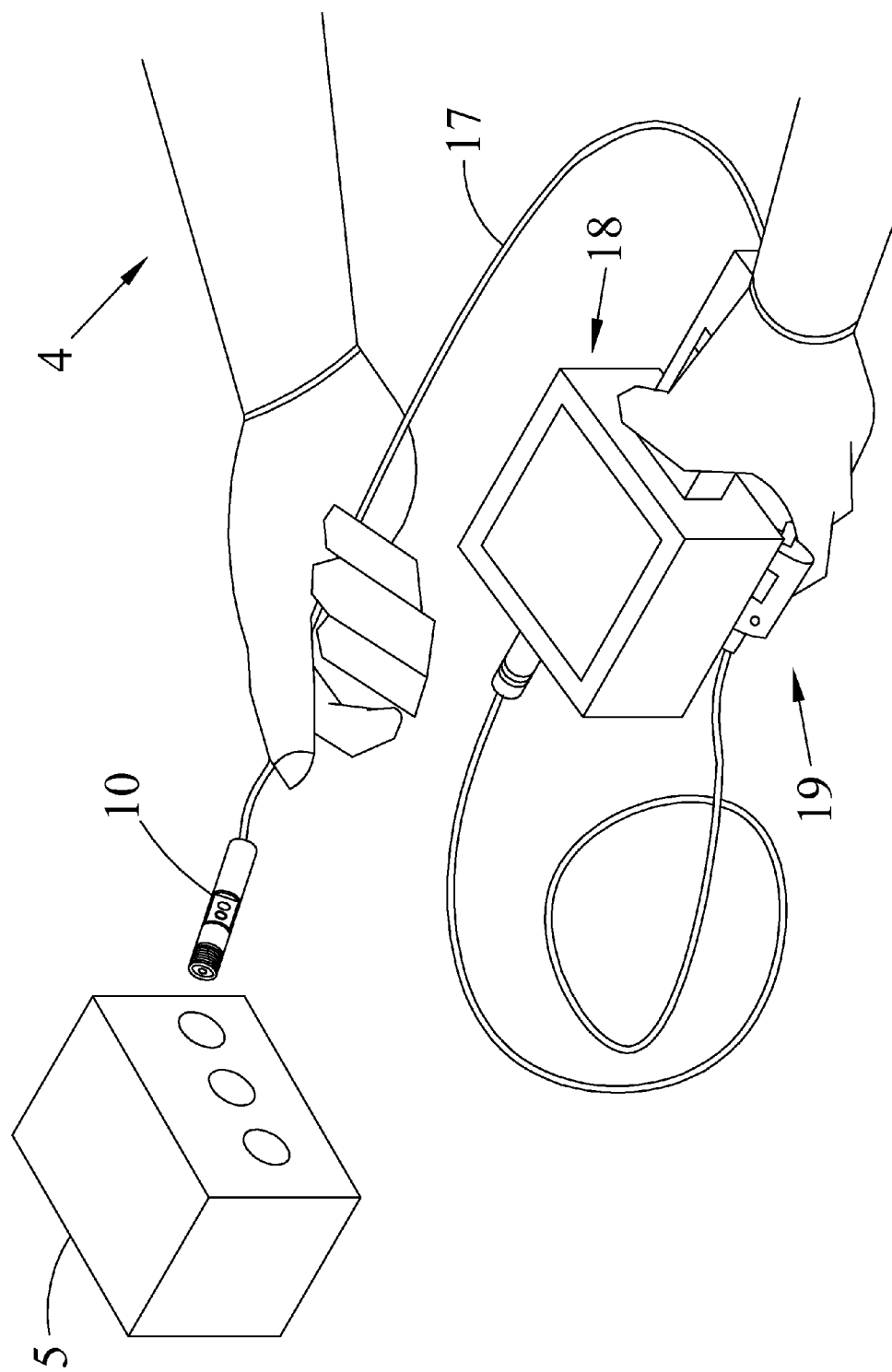
FIG. 6 is a schematic view showing the use of a is preferred embodiment of an endoscope apparatus according to the present invention.

In order to explain the use of the present invention, simultaneously referring to FIGS. 1-7, as shown in FIG. 6, there is shown a schematic view showing the use of an endoscope apparatus according to the present invention. If the user 4 wants to observe the interior of an object 5 having a smaller internal depth to be inspected by the endoscope apparatus 1 according to the present invention, the hose 17 between the switch 19 and the tube body 10 can be coiled up and held in a hand to insert the tube body 10 into the interior of the object 5 to be inspected and the holding part 18 is held by the other hand. At this time, both of the first light-emitting device 120 and the second light-emitting device 140 are lighted up (or either of them may be optionally lighted up). The first lens 121 collects a reflected light 21 with a first viewing angle reflected by the object 5 and transmits it to the first image sensor 122. The first image sensor 122 receives the reflected light 21 and then provides a first image signal to the first flexible PCB 13 according to the reflected light 21. The second lens 141 collects the other reflected light 22 with a second viewing angle reflected by the object 5 simultaneously and transmits it to the second image sensor 142. The second image sensor 142 receives the reflected light 22 and then provides a second image signal to the first flexible PCB 13 according to the reflected light 22. At this time, the user 4 can press the switch 19 to control the switching module 130 that allows the first image signal or the second image signal to be outputted to the second flexible PCB 16. The user 4 can distinguish that the picture currently displayed on the display unit 181 corresponds to which angle of view by the indicator lights 190, 191. After received by the second flexible PCB 16, the first image signal or the second image signal is transmitted via the conducting wire 170 to the printed circuit board 180 of the holding part 18. Then, the printed circuit board 180 controls the display unit 181 that displays the corresponding picture. The picture which is preset to be displayed on the display unit 181 of the holding part 18 may be a picture with the first angle of view or a picture with the second angle of view. In this embodiment, the first angle of view is an angle of view on the end toward the front of the tube body 10, and the second angle of view is an angle of view on the side of the tube body 10.

Figure 7:
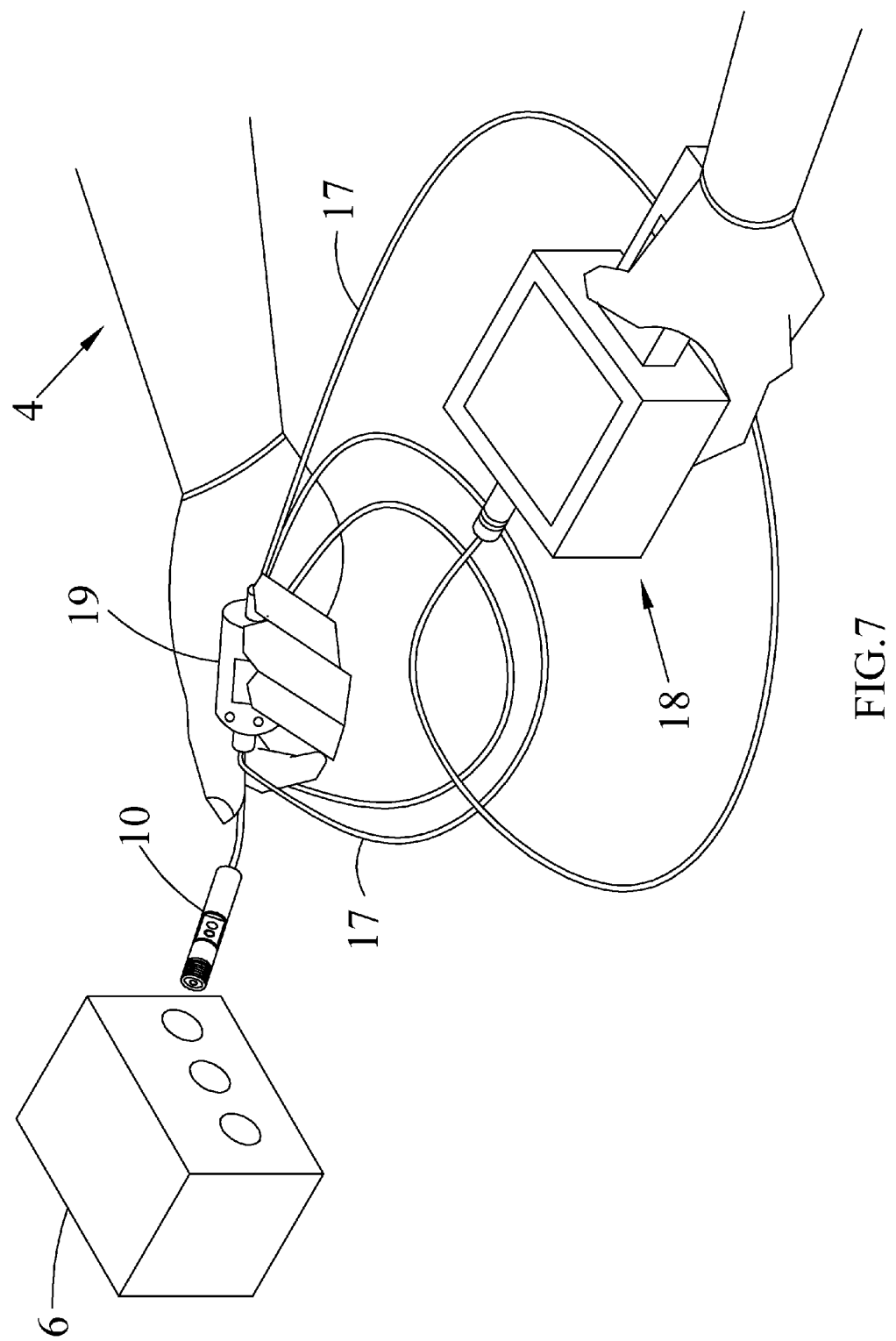
FIG. 7 is a schematic view of another preferred embodiment of an endoscope apparatus according to the present invention.

Moreover, as shown in FIG. 7, if the user 4 wants to observe the interior of an object 6 having a larger internal depth to be inspected by the endoscope apparatus 1 according to the present invention, the hose 17 between the switch 19 and the holding part 18 can be coiled up and the switch 19 can be attached to the back of the holding part, for example, by Velcro. Afterwards, the hand holds the holding part 18 and simultaneously controls the switch 19 that switches pictures of the different angles of view, and the other hand controls the hose between the tube body 10 and the switch 19 and inserts it into the interior of the object 6 to be inspected, so as to observe the interior of the object 6 having a larger internal depth to be inspected. In addition, the operation of all components is the same as described above and will be explained in no more details.

Figure 8:
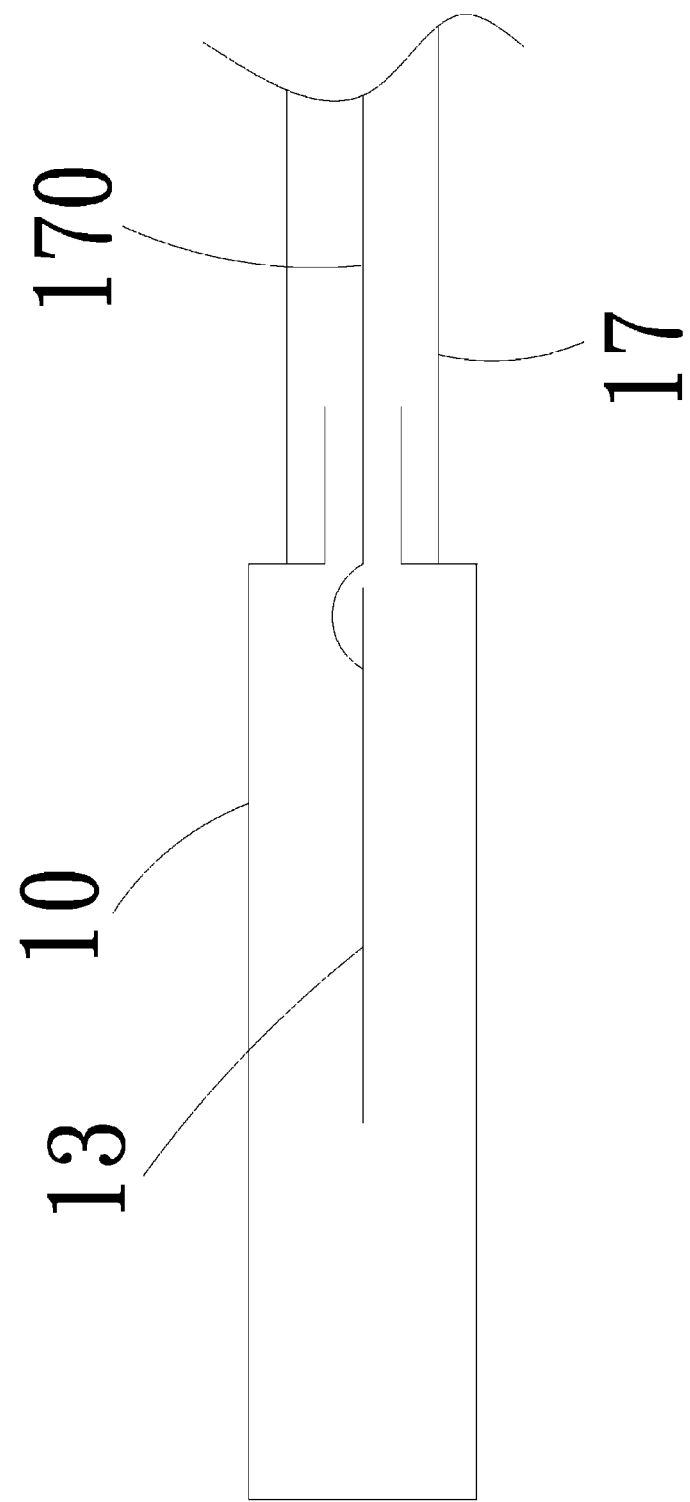
FIG. 8 is another schematic view of a tube body of an endoscope apparatus according to the present invention.

Furthermore, except the embodiments of the assembly of the tube body and the connecting tube as shown in FIG. 3 and FIG. 4, the present invention still comprises another embodiment, as shown in FIG. 8, which is another schematic view of a tube body of an endoscope apparatus according to the present invention. In this embodiment, the first flexible PCB 13 is connected to the conducting wire 170 directly. By this way, the cube body is connected to the hose 17. Besides, the operations of each part of the endoscope of the present invention are the same with those abovementioned, thus it will not be stated here again.

The endoscope apparatus of the present invention captures images with different angles, so as to increase convenience of observing an object to be inspected with an endoscope apparatus. The problem of difficulty in assembly of an endoscope apparatus having a small tube diameter can be solved by the assembly of multiple components.

The above description is illustrative only and is not to be considered limiting. Various modifications or changes can be made without departing from the spirit and scope of the invention. All such equivalent modifications and changes shall be included within the scope of the appended claims.

What is claimed is:
1. An endoscope apparatus comprising:
   a tube body, one end of the tube body being connected with an accommodating part;
   a first image capture module disposed inside the accommodating part, comprising:
      at least a first light-emitting device arranged for emitting light to irradiate an object;
      a first lens arranged for collecting a reflected light with a first viewing angle reflected by the object; and
      a first image sensor disposed facing the first lens and adjacent to the first light-emitting device for receiving the reflected light and providing a first image signal according to the reflected light;
   a first flexible printed circuit board (PCB) disposed inside the tube body, connected with the first image capture module; and
   a second image capture module disposed inside the tube body, connected with the first flexible PCB, comprising:
      at least a second light-emitting device, emitting light to irradiate the object;
      a second lens, collecting other reflected light with a second viewing angle reflected by the object; and
      a second image sensor disposed facing the second lens and the at least a second light-emitting device for receiving the other reflected light and providing a second image signal according to the other reflected light;
   wherein the first flexible PCB is further provided with a switching module for switching the first image signal or the second image signal to be outputted to a second flexible PCB.
2. The endoscope apparatus as recited in claim 1, wherein the endoscope apparatus further comprises:
   a notch, disposed on one side near one end of the tube body; and
   a cover, disposed on the notch of the tube body, the cover having a first opening and a second opening;
   wherein, the second light-emitting device is disposed below the first opening, and the second lens is disposed below the second opening.
3. The endoscope apparatus as recited in claim 1, wherein the endoscope apparatus further comprises:
   a connecting tube, one end of the connecting tube being connected with the other end of the tube body, the diameter of the end of the connecting tube being different from the diameter of the other end of the connecting tube; and
   a second flexible PCB disposed inside the connecting tube;
   wherein the end of the connecting tube is connected with the other end of the tube body via the connection between the first flexible PCB and the second flexible PCB.
4. The endoscope apparatus as recited in claim 3, wherein the first flexible PCB is further provided with a switching module for switching the first image signal or the second image signal to be outputted to the second flexible PCB.

5. The endoscope apparatus as recited in claim 4, further comprising:
   a hose connected with the other end of the connecting tube, at least a conducting wire being further disposed inside the hose, and the at least a conducting wire being connected with the second flexible PCB to transmit the first image signal or the second image signal;
   a holding part connected with the connecting tube via the hose; and
   a switch having a plurality of indicator lights and connected with the at least a conducting wire, and the switch being disposed on the hose and located between the connecting tube and the holding part for controlling the switching module.

6. The endoscope apparatus as recited in claim 5, wherein the holding part further comprises:
   a printed circuit board, and the printed circuit board is disposed inside the holding part and connected with the second flexible PCB via the at least a conducting wire for receiving the first image signal or the second image signal; and
   a display unit, and the display unit is disposed on the holding part and connected with the printed circuit board for receiving the first image signal or the second image signal to display the image with the first angle of view or the image with the second angle of view.

7. The endoscope apparatus as recited in claim 1, further comprising:
   a hose connected with the other end of the tube body, at least a conducting wire being further disposed inside the hose, and the at least a conducting wire being connected with the first flexible PCB to transmit the first image signal or the second image signal;
   a holding part connected with the tube body via the hose; and
   a switch having a plurality of indicator lights and connected with the at least a conducting wire, and the switch being disposed on the hose and located between the tube body and the holding part for controlling the switching module.

8. The endoscope apparatus as recited in claim 7, wherein the holding part further comprises:
   a printed circuit board, and the printed circuit board is disposed inside the holding part and connected with the first flexible PCB via the at least a conducting wire for receiving the first image signal or the second image signal; and
   a display unit, and the display unit is disposed on the holding part and connected with the printed circuit board for receiving the first image signal or the second image signal to display the image with the first angle of view or the image with the second angle of view.

9. The endoscope apparatus as recited in claim 1, wherein the first light-emitting device and the second light-emitting device are light-emitting diodes (LED), and the first light-emitting device and the second light-emitting device emit white light, red light, blue light, infrared light or ultraviolet light.

* * * * *